United States Patent
Jang et al.

(10) Patent No.: US 7,505,155 B2
(45) Date of Patent: Mar. 17, 2009

(54) APPARATUS AND METHOD FOR INSPECTING POLY-SILICON

(75) Inventors: Keun-Ho Jang, Seoul (KR); Hyun-Gue Kim, Seoul (KR)

(73) Assignee: Samsung Mobile Display Co., Ltd., Suwon (KR)

( * ) Notice: Subject to any disclaimer, the term of this patent is extended or adjusted under 35 U.S.C. 154(b) by 554 days.

(21) Appl. No.: 11/038,030

(22) Filed: Jan. 21, 2005

(65) Prior Publication Data
US 2005/0174569 A1 Aug. 11, 2005

(30) Foreign Application Priority Data
Feb. 11, 2004 (KR) .................. 10-2004-0009126

(51) Int. Cl.
*G01B 11/06* (2006.01)
(52) U.S. Cl. .................. 356/634; 356/635
(58) Field of Classification Search .......... 356/634, 356/635; 250/559.19
See application file for complete search history.

(56) References Cited

U.S. PATENT DOCUMENTS 5,739,909 A * 4/1998 Blayo et al. .................. 356/369

FOREIGN PATENT DOCUMENTS

| JP | 2001-196430 | 7/2001 |
| JP | 2002-277216 | 9/2002 |
| JP | 2003-318240 | 11/2003 |

OTHER PUBLICATIONS

Rigaku Corporation, X-Ray Research Institutes; Handbook of X-Ray Diffraction; pp. 66-68, 76; Published in Japan on Aug. 15, 1996.

* cited by examiner

*Primary Examiner*—Roy M Punnoose
(74) *Attorney, Agent, or Firm*—H.C. Park & Associates, PLC

(57) ABSTRACT

An apparatus and method for inspecting polycrystalline silicon (Poly-Si) that illuminates light onto protrusions in the Poly-Si in order to determine a distance between them using intensity and reflection angle of reflected light. The Poly-Si inspection apparatus includes a light source that illuminates light, and a reflected light detector for receiving reflected light, wherein a distance between protrusions is measured by an incident angle of the light illuminated into the protrusion from the light source, a detection angle of the reflected light detector, and a wavelength of the detected reflected light.

16 Claims, 6 Drawing Sheets

APPARATUS AND METHOD FOR INSPECTING POLY-SILICON

CROSS-REFERENCE TO RELATED APPLICATION

This application claims priority to and the benefit of Korean Patent Application No. 10-2004-0009126, filed Feb. 11, 2004, which is hereby incorporated by reference for all purposes as if fully set forth herein.

BACKGROUND OF THE INVENTION

1. Field of the Invention

The present invention relates to an inspection apparatus and, more particularly, to an apparatus and method for inspecting polycrystalline silicon (Poly-Si) using illuminated and reflected light.

2. Discussion of the Background

Generally, a thin film transistor (TFT) comprising Poly-Si has about 10 to 100 times mobility of a TFT comprising amorphous silicon (a-Si). Therefore, the Poly-Si TFT is typically used for a pixel switching device and for a peripheral driving circuit in a liquid crystal display (LCD) and organic EL display devices, allowing development of an integrated TFT-LCD with simultaneously formed pixel and driving circuit TFTs on the same substrate. FIG. 1 shows a TFT that may be used in an integrated LCD or organic EL display device.

FIG. 1 is a cross-sectional view illustrating a typical TFT.

Referring to FIG. 1, a buffer layer 2, made of an insulating material such as silicon oxide ($SiO_2$), is formed on an insulating substrate 1, and a semiconductor layer, made of Poly-Si with a mean grain diameter of 0.24 μm~0.45 μm, is formed on the buffer layer 2. Implanting impurities in the semiconductor layer forms a channel 3 and drain and source regions 4 and 5.

A gate insulating layer 6 is formed on the entire surface of the semiconductor layer, and an interlayer insulating layer 7 is formed on the gate insulating layer 6. Drain and source electrodes 10 and 9 are connected to the drain and source regions 4 and 5 via contact holes 12 and 11, respectively. A gate electrode 8 is formed on the gate insulating layer 6 over the channel 3.

The Poly-Si forming the semiconductor layer may include various sized grains in a range of several nm to μm by means of an excimer laser annealing (ELA) process. Protrusions (P and P' in FIG. 2A and FIG. 2B, respectively) may be formed in the Poly-Si grain boundary based on the crystallization method.

FIG. 2A shows the formed protrusions P having a consistent interval therebetween, and FIG. 2B shows the formed protrusions P' having an inconsistent interval therebetween.

When displaying an image on an organic EL display device or an LCD device fabricated with Poly-Si having inconsistently formed protrusions as shown in FIG. 2B, a plurality of thin stripes may be generated on the screen, thereby deteriorating image quality. On the other hand, fabricating a display device using Poly-Si having consistently formed protrusions, as shown in FIG. 2A, may significantly reduce the stripes.

Therefore, good and bad quality products may be identified by measuring the distance between the Poly-Si protrusions. Therefore, an inspection apparatus that is capable of measuring the distance between the Poly-Si protrusions is desired.

SUMMARY OF THE INVENTION

The present invention provides an apparatus and method for inspecting Poly-Si that may be identify good and bad quality products by illuminating a light onto Poly-Si and measuring a distance between protrusions using wavelength and intensity of the diffracted-reflected light.

Additional features of the invention will be set forth in the description which follows, and in part will be apparent from the description, or may be learned by practice of the invention.

The present invention discloses an apparatus for inspecting Poly-Si including a light source that illuminates light, and a reflected light detector for receiving reflected light. A distance between protrusions is determined using an incident angle of light illuminated onto the protrusions, a detection angle of the reflected light detector, and a wavelength of detected reflected light.

The present invention also discloses an apparatus for inspecting Poly-Si with a plurality of protrusions including a measuring member having a light source that illuminates light, a light source controller for controlling an incident angle of the light, a reflected light detector for receiving reflected light, a detection angle controller for controlling a detection angle of the reflected light detector, and a measuring substrate on which the Poly-Si is loaded. A support member includes a first support for supporting the measuring substrate and a first fastener for fixing the first support to support the measuring member, wherein distances between the protrusions are calculated by the following equation:

$$m\lambda = d(\sin \alpha + \sin \beta)$$

where m is an integer, $\lambda$ is a wavelength of reflected light, d is a distance between protrusions, $\alpha$ is an incident angle, and $\beta$ is a detection angle.

The present invention also discloses a method for inspecting Poly-Si comprising determining a distance between protrusions in the Poly-Si by illuminating light onto the protrusions.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

Figure 1:
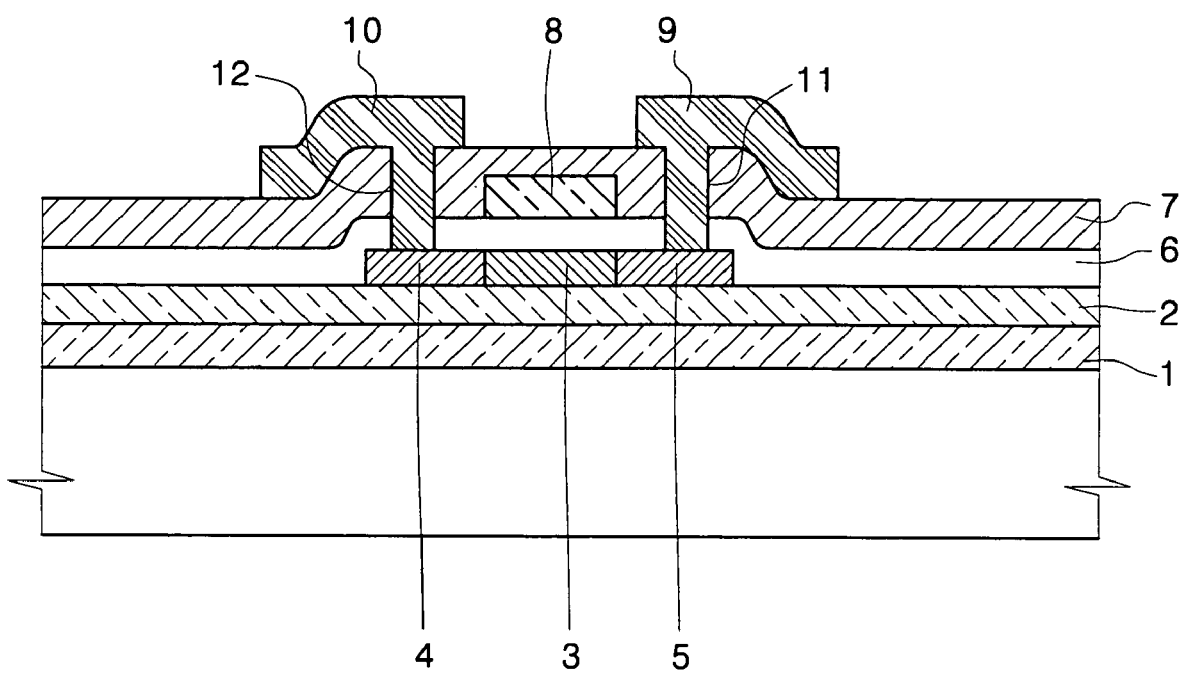
FIG. 1 is a cross-sectional view illustrating a typical TFT.
Figure 2A:
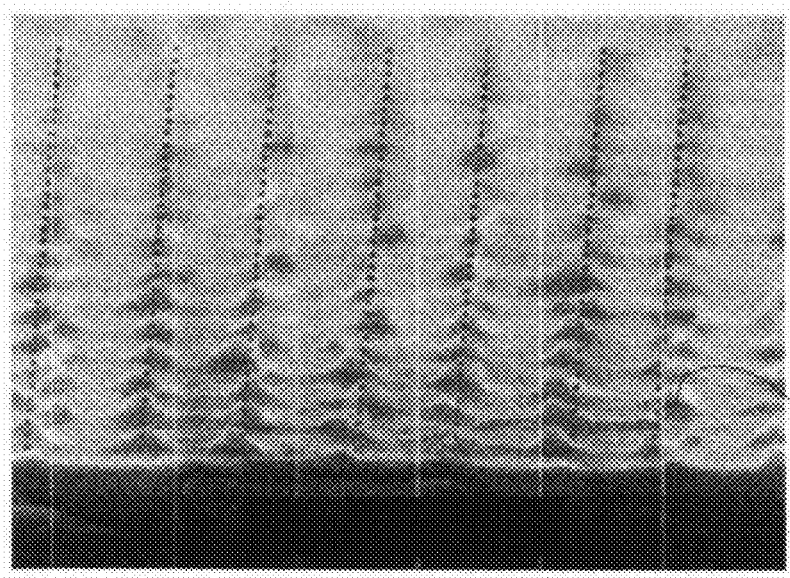
FIG. 2A is a perspective view showing an example of Poly-Si.
Figure 2B:
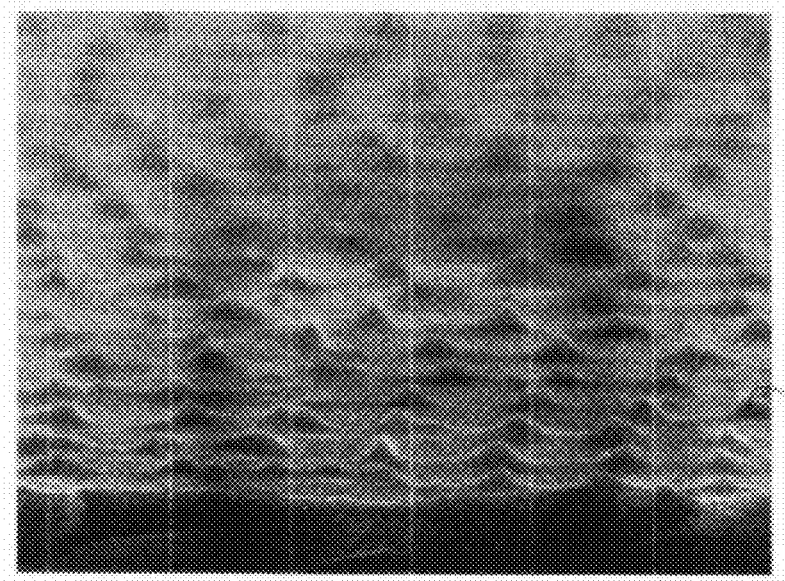
FIG. 2B is a perspective view showing another example of Poly-Si.

The present invention will now be described more fully hereinafter with reference to the accompanying drawings showing exemplary embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions are exaggerated for clarity. Like numbers refer to like elements throughout the specification.

Figure 3:
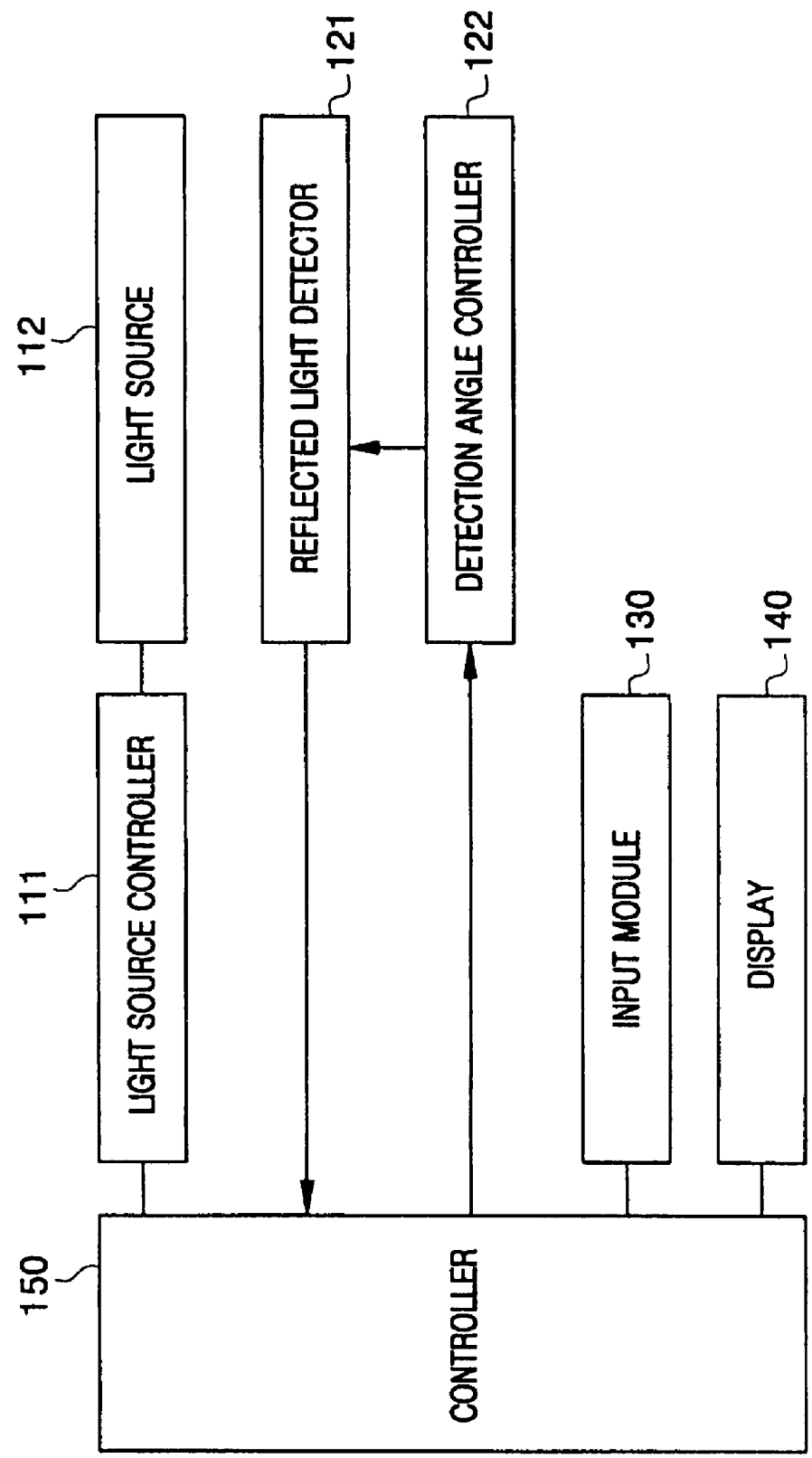
FIG. 3 is a block diagram of an apparatus for inspecting Poly-Si in accordance with an exemplary embodiment of the present invention.

FIG. 3 is a block diagram of an apparatus for inspecting Poly-Si in accordance with an exemplary embodiment of the present invention.

A light source 112 emits a predetermined light, and a light source controller 111 controls a view angle of the light source 112 and intensity of the emitted light. A reflected light detector 121 detects the reflected light, and a detection angle controller 122 controls a view angle of the reflected light detector 121. Further, an input module 130 transmits a user control signal, and a display 140 displays measured data. A controller 150 controls the light source controller 111 and the detection angle controller 122 based on the user control signal transmitted from the input module 130.

Referring to FIG. 3, when the user transmits the user control signal through the input module 130, the controller 150 outputs control signals to the detection angle controller 122 and the light source controller 111 based on the user control signal.

Therefore, the light source controller 111 may adjust a view angle of the light source 112 to a predetermined angle based on the control signal of the controller 150, and it drives the light source 112 to emit light at a predetermined intensity. Additionally, the detection angle controller 122 adjusts a view angle of the reflected light detector 121 to a predetermined angle based on the control signal of the controller 150.

The light source 112 illuminates white light, for example, to a protrusion P of the Poly-Si, and the reflected light detector 121 detects light that is reflected from the protrusion P. The reflected light detector 121 also calculates a distance between protrusions using a detection angle and wavelength intensity of the reflected light and an incident angle of the illuminated light, and transmits the calculated distance to the controller 150.

The controller 150 then transmits the calculated distance to the display 140, which displays it.

Figure 4:
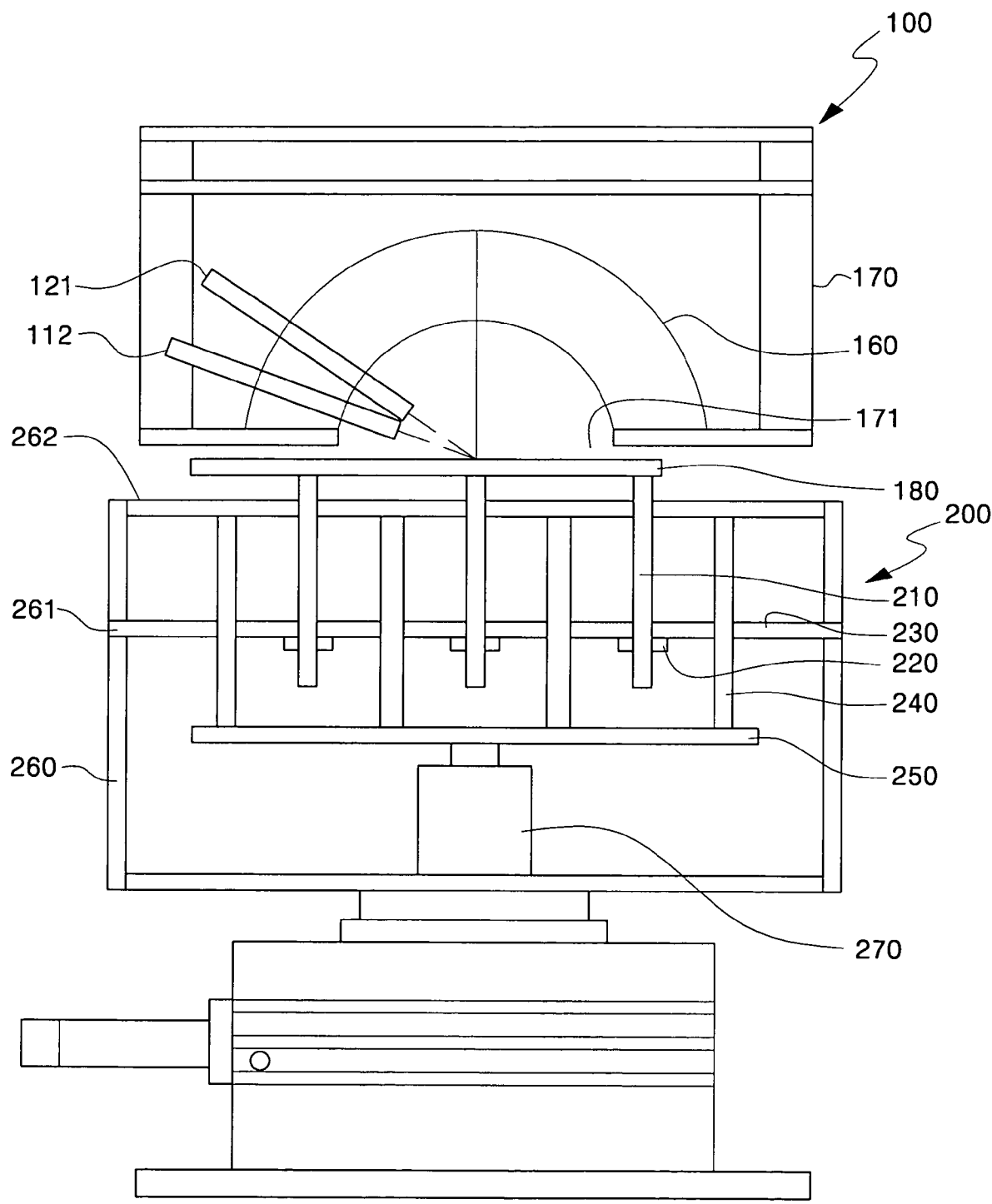
FIG. 4 is a cross-sectional view of an apparatus for inspecting Poly-Si in accordance with an exemplary embodiment of the present invention.

FIG. 4 is a cross-sectional view showing an apparatus for inspecting Poly-Si in accordance with an exemplary embodiment of the present invention.

Referring to FIG. 4, the Poly-Si inspection apparatus includes: a measuring member 100 having the light source 112, the reflected light detector 121, an angle meter 160 that measures a view angle of the light source 112 and the reflected light detector 121, and a measuring substrate 180 on which the Poly-Si is loaded; and a support member 200 including a plurality of supports and fasteners supporting the measuring member 100.

The measuring member 100 has a predetermined shape and includes a body 170 having the light source 112, the reflected light detector 121, and the angle meter 160. The body 170 has an opening 171 exposing the measuring substrate 180. The measuring substrate 180 may be formed below the opening 171, and the light source 112 and the reflected light detector 121 are set up toward the measuring substrate 180 at a predetermined angle on one side in the body 170. The angle meter 160 may be fixed in the body 170.

The support member 200 may include a main body 260 having a predetermined shape, a first support 210 for supporting the measuring substrate 180, and a first fastener 220 for fixing the first support 210.

A second support 230, which may be fixed in a row at a predetermined position in the support member body 260, is formed, and the first support 210 has one side connected to the bottom surface of the measuring substrate 180 and the other side passing through the second support 230 and fixed by the first fastener 220. A third support 240, which may pass through the second support 230, may be included having one side connected to the top surface 262 of the support member body 260 and the other side fixed to the second fastener 250 to support the top surface 262 and the first support 210. The third support 240 may be fixed to a top surface of the second fastener 250, and a bottom surface of the second fastener 250 may be coupled to a supporting axis 270.

It may be preferable to have the measuring substrate 180 be rotatable, which may be accomplished by arranging the supporting axis 270 to be rotatable. In this case, the supporting axis 270 may be a rotating axis having one side connected to a motor in order to rotate the second fastener 250. Further, the second support 230 may be formed in a separate shape so that the first support 210 and the third support 240 are rotatable, or a circular rotational groove may be formed in a joint 261 where the second support 230 is coupled to the support member body 260.

Figure 5:
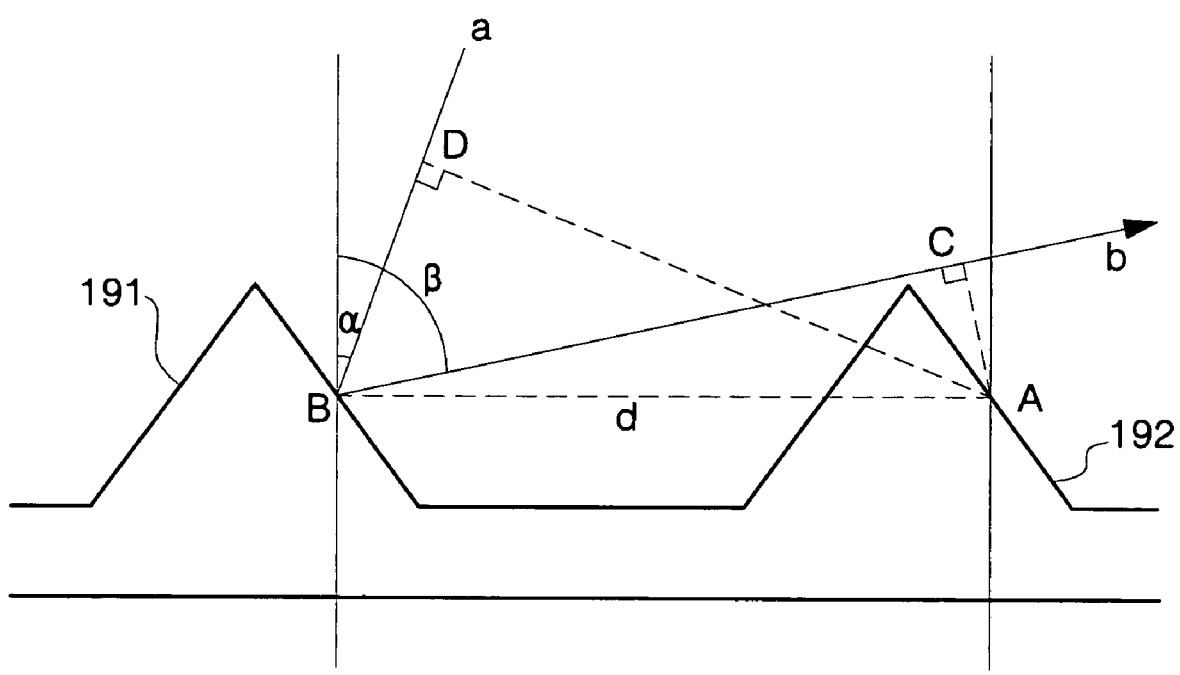
FIG. 5 is a cross-sectional view showing a method of measuring a distance between Poly-Si protrusions in accordance with an exemplary embodiment of the present invention.

FIG. 5 is a cross-sectional view showing a method of measuring a distance between Poly-Si protrusions in accordance with an exemplary embodiment of the present invention.

Referring to FIG. 5, light emitted from a light source 112, e.g., white light, is illuminated with a certain incident angle α at a predetermined position of a first protrusion 191. This illuminated light is reflected, and the reflected light detector 121 detects reflected light having a predetermined reflection angle β beyond a peak position of a second protrusion 192.

In other words, when a plurality of protrusions are arranged in a consistent interval, if light is illuminated onto Poly-Si as described above, diffraction by reflection may occur, so that the reflected light detector 121 receives the diffracted reflected light to measure intensity and wavelength of the reflected light.

The reflected light detector 121 then uses an incident angle α of an incident light from the light source 112, a detection angle β of a reflected light, and a wavelength λ of the reflected light to measure a distance d between the first and second protrusions 191 and 192. This measurement may be calculated by the following equation:

$$m\lambda = BD + BC = d(\sin \alpha + \sin \beta)$$

where m is an integer, λ is a wavelength of the reflected light, d is a distance between protrusions, α is an incident angle, and β is a detection angle. Additionally, BD is a distance between positions B and D, and BC is a distance between positions B and C.

The position B is where light is incident on the first protrusion 191. The position D is perpendicular to a position A of the second protrusion 192 on an optical axis a of the light incident on the first protrusion 191. The position C is on an optical axis b of the light reflected from the position B toward the second protrusion 192 and perpendicular to the position A. The distances BD and BC are summed to calculate an optical path difference, where the optical path difference is a product of a wavelength and a constant integer m, which results in mλ, in the above equation.

In other words, when a predetermined light is illuminated onto a plurality of protrusions, light reflected from each protrusion travels along the optical axis b and may be subjected to constructive interference that may be amplified by the light reflected from an adjacent protrusion for, where the amplified light becomes by integer (m) times, and the optical path difference may be calculated using the wavelength λ and the integer m based on the constructive interference. Here, the incident angle α should be at least 43° so that intensity of diffracted light detected by the reflected light detector 121 may be relatively high.

Further, BD is a product of the distance d between the protrusions 191 and 192, i.e., AB, and the sine of the incident angle α, and BC is a product of the distance d between the protrusions 191 and 192, and the sine of the detection angle β.

Figure 6:
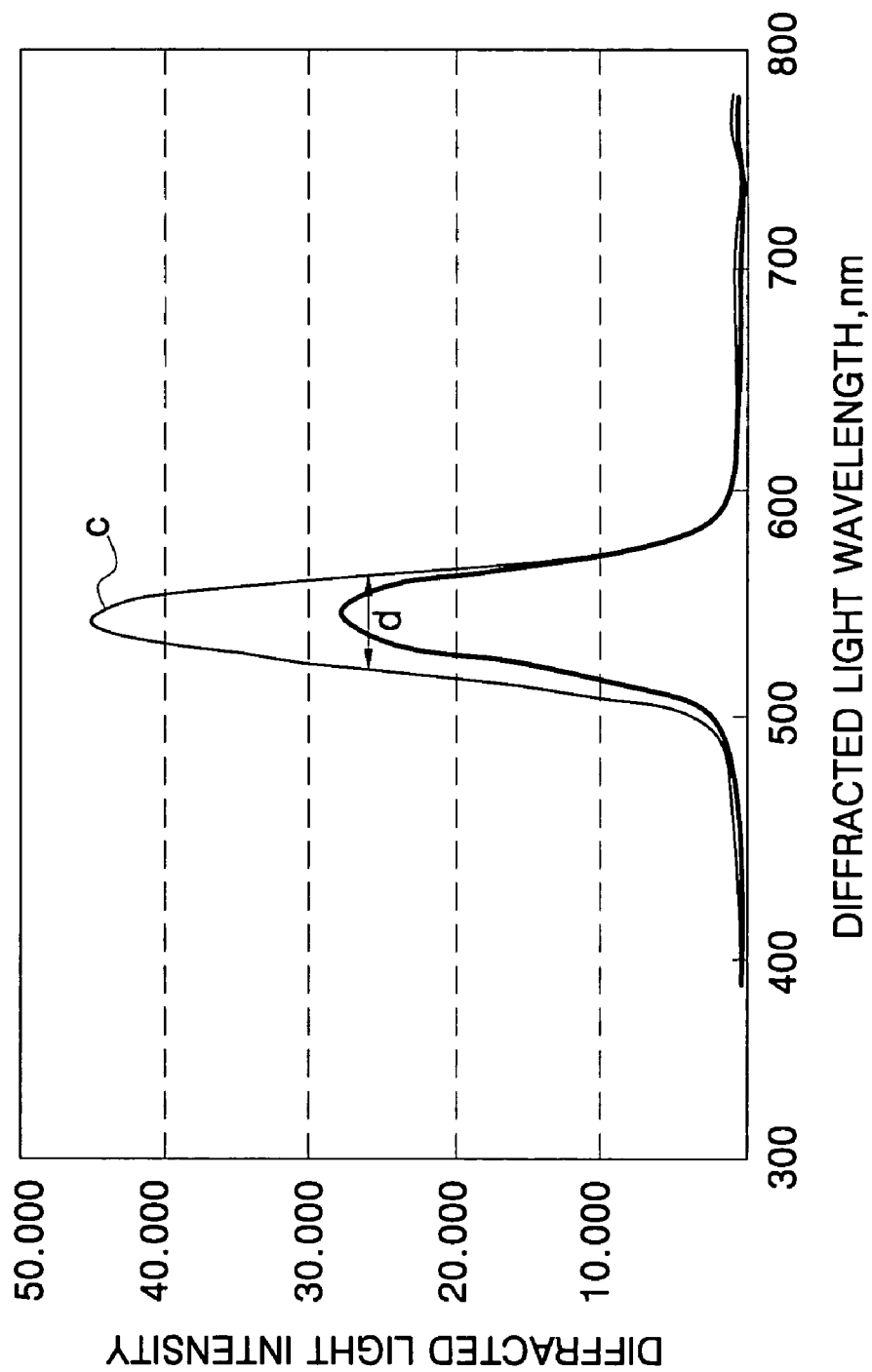
FIG. 6 is a graph showing optical characteristics of good and bad quality products in accordance with an exemplary embodiment of the present invention.

FIG. 6 is a graph showing the optical characteristics of good and poor quality products in accordance with an exemplary embodiment of the present invention.

FIG. 6 shows a spectrum measured by illuminating light onto Poly-Si with a diffracted light intensity as Y-axis, and a diffracted light wavelength as X-axis. The good quality product, which has a plurality of consistently spaced protrusions 191 and 192, has a strong diffracted light intensity as compared with a poor quality product having a plurality of inconsistently spaced protrusions.

Specifically, when light is illuminated to each of the plurality of protrusions 191 and 192 and the reflected light is received as described above, a constructive interference caused by the diffracted light occurs at each adjacent protrusion 191 and 192. Thus, as the distance d between the protrusions 191 and 192 becomes uniform, intensity of reflected light diffracted from the Poly-Si increases. Additionally, when the distance d between each protrusion 191 and 192 is within a predetermined range, diffracted light having the same wavelength may be reflected. Alternatively, when there is a difference in the distance d between each protrusion 191 and 192, diffracted light having different wavelengths may be reflected. Hence, as shown in FIG. 6, a peak value c in the spectrum becomes an average of the distance d between the protrusions.

In other words, FIG. 6 shows diffracted light intensity and wavelength based on the distance between the protrusions, where as the number of Poly-Si protrusions having a distance within a predetermined range increases, diffracted light having the same wavelength is produced, and as diffracted light having the same wavelength increases, light intensity at a specific wavelength increases due to the constructive interference. Therefore, a range having the maximum number of distances d within a given range may become a peak value c of FIG. 6.

Further, when there is a difference in the distance d between the protrusions 191 and 192, a difference between the wavelengths of the diffracted reflected light occurs, so that light having a certain range of wavelength band in the spectrum forms a distribution with a predetermined range, i.e., full width at half maximum (FWHM).

As describe above, according to an apparatus and method for inspecting Poly-Si of exemplary embodiments of the present invention, a predetermined light is illuminated to measure a distance between protrusions to identify good or bad quality products, thereby preventing failures from occurring in the display device and improving reliability.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An apparatus for inspecting polycrystalline silicon (Poly-Si), comprising:
    a light source to illuminate a protrusion; and
    a reflected light detector for receiving reflected light,
    wherein a distance between protrusions is determined using an incident angle of light illuminated onto the protrusions, a detection angle of the reflected light detector, and a wavelength of detected reflected light.

2. The apparatus of claim 1, wherein the distance between the protrusions is calculated by the following equation:

$$m\lambda = d(\sin\alpha + \sin\beta)$$

where m is an integer, λ is a wavelength of reflected light, d is a distance between protrusions, α is an incident angle, and β is a detection angle.

3. The apparatus of claim 1, further comprising:
    a light source controller for controlling an incident angle of the light source; and
    a detection angle controller for controlling the detection angle of the reflected light detector.

4. The apparatus of claim 1, wherein an average value of distances between the protrusions is measured by a peak center in an intensity spectrum over a wavelength of light reflected and diffracted from the protrusions.

5. The apparatus of claim 1, wherein a distribution of distances between the protrusions is measured by peak full width at half maximum in an intensity spectrum over a wavelength of light reflected and diffracted from the protrusions.

6. The apparatus of claim 1, wherein the incident angle of the light illuminated from the light source onto the protrusions is at least 43°.

7. An apparatus for inspecting polycrystalline silicon (Poly-Si) with a plurality of protrusions, comprising:
    a measuring member having a light source to emit light that illuminates a protrusion, a light source controller for controlling an incident angle of the light, a reflected light detector for receiving reflected light, a detection angle controller for controlling a detection angle of the reflected light detector, and a measuring substrate on which the Poly-Si is loaded; and
    a support member comprising a first support for supporting the measuring substrate and a first fastener for fixing the first support to support the measuring member,
    wherein distances between protrusions are calculated by the following equation:

$$m\lambda = d(\sin\alpha + \sin\beta)$$

where m is an integer, λ is a wavelength of reflected light, d is a distance between protrusions, α is an incident angle, and β is a detection angle.

8. The apparatus of claim 7, wherein the measuring member further comprises an angle meter for measuring a view angle of the reflected light detector and the light source.

9. The apparatus of claim 7, wherein the light source emits white light.

10. The apparatus of claim 7, wherein an average value of the distances between the protrusions is measured by a peak center in an intensity spectrum over a wavelength of light reflected and diffracted from the protrusions.

11. The apparatus of claim 7, wherein a distribution of the distances between the protrusions is measured by peak full width at half maximum in an intensity spectrum over a wavelength of light reflected and diffracted from the protrusions.

12. The apparatus of claim 7, wherein the incident angle of the light illuminated from the light source to the protrusions is at least 43°.

13. A method for inspecting polycrystalline silicon (Poly-Si), comprising:
   determining a distance between protrusions in the Poly-Si by illuminating light onto the protrusions,
   wherein the distance between protrusions is determined using an incident angle of the light illuminated onto the protrusions, a detection angle of reflected light, and a wavelength of the reflected light.

14. The method of claim 13, wherein the distance between protrusions is calculated by the following equation:

$$m\lambda = d(\sin \alpha + \sin \beta)$$

where m is an integer, $\lambda$ is the wavelength of the reflected light, d is the distance between protrusions, $\alpha$ is the incident angle, $\beta$ is the detection angle.

15. The method of claim 14, further comprising:
   measuring an average value of the distances between the protrusions through a peak center in an intensity spectrum over a wavelength of light reflected and diffracted from the protrusions; and
   measuring a distribution of the distances between the protrusions through peak full width at half maximum in the intensity spectrum over the wavelength of the light reflected and diffracted from the protrusions.

16. The method of claim 14, wherein the incident angle of the light illuminated onto the protrusion is at least 43°.

* * * * *